US008697841B2

(12) United States Patent
Lu et al.

(10) Patent No.: US 8,697,841 B2
(45) Date of Patent: Apr. 15, 2014

(54) PEPTIDE FOR TRANSMIGRATION ACROSS BLOOD BRAIN BARRIER AND DELIVERY SYSTEMS COMPRISING THE SAME

(75) Inventors: Maggie J. M. Lu, Hsinchu County (TW); Hsiang-Fa Liang, Taipei County (TW); Shing-Ming Cheng, Changhua County (TW); Yi-Ju Ko, Taipei County (TW); Li-Wen Chang, Taoyuan County (TW)

(73) Assignee: Industrial Technology Research Institute, Hsinchu (TW)

( * ) Notice: Subject to any disclaimer, the term of this patent is extended or adjusted under 35 U.S.C. 154(b) by 434 days.

(21) Appl. No.: 12/979,804

(22) Filed: Dec. 28, 2010

(65) Prior Publication Data

US 2011/0165079 A1    Jul. 7, 2011

Related U.S. Application Data

(60) Provisional application No. 61/291,334, filed on Dec. 30, 2009.

(51) Int. Cl.
| | | |
|---|---|---|
| C07K 7/08 | (2006.01) | |
| A61K 38/10 | (2006.01) | |
| C07K 17/02 | (2006.01) | |
| C07K 17/14 | (2006.01) | |

(52) U.S. Cl.
USPC ............................. 530/327; 514/1.2; 514/21.5

(58) Field of Classification Search
USPC ................................... 530/327; 514/1.2, 21.5
See application file for complete search history.

(56) References Cited

U.S. PATENT DOCUMENTS

| | | | |
|---|---|---|---|
| 5,977,307 A | 11/1999 | Friden et al. | |
| 7,514,402 B2 | 4/2009 | Nelson et al. | |
| 2004/0001801 A1* | 1/2004 | Madison et al. | 424/85.1 |
| 2005/0208558 A1* | 9/2005 | Venter et al. | 435/6 |
| 2006/0039859 A1 | 2/2006 | Sharma et al. | |

FOREIGN PATENT DOCUMENTS

WO    WO 98/22092 A1    5/1998

OTHER PUBLICATIONS

Unzueta et al., 2012, Non-amyloidogenic peptide tags for the regulatable self-assembling of protein-only nanoparticles, Biomaterials, 33: 8714-8722.*
Qin et al., 2011, Identification of a LNCaP-Specific Binding Peptide Using Phage Display, Pharm. Res., 28: 2422-2434.*
Banks et al., "Passage of Peptides Across the Blood-Brain Barrier: Pathophysiological Perspectives", Life Sciences, vol. 59, No. 23, 1996, pp. 1923-1943.
Begley, "Delivery of therapeutic agents to the central nervous system: the problems and the possibilities", Pharmacology & Therapeutics, vol. 104, 2004, pp. 29-45.
Cerletti et al., "Endocytosis and Transcytosis of an Immunoliposome-Based Brain Drug Delivery System", Journal of Drug Targeting, 2000, vol. 8, No. 6, pp. 435-446.
Gaillard et al., "Establishment and functional characterization of an in vitro model of the blood-brain barrier, comprising a co-culture of brain capillary endothelial cells and astrocytes", European Journal of Pharmaceutical Sciences, vol. 12, No. 3, 2001, pp. 215-222.
Hsu et al., "In Vivo Near-Infrared Fluorescence Imaging of Integrin alphavbeta3 in an Orthotopic Glioblastoma Model", Mol Imaging Biol, vol. 8, No. 6, 2006, pp. 315-323.
Kataoka et al., "Block copolymer micelles for drug delivery: design, characterization and biological significance", Advanced Drug Delivery Reviews, vol. 47, No. 1, pp. 113-131, 2001.
Lagrange et al., "Transendothelial Permeability Changes Induced by Free Radicals in an In Vitro Model of the Blood-Brain Barrier", Free Radical Biology & Medicine, vol. 27, Nos. 5/6, 1999, pp. 667-672.
Lee et al., "Receptor mediated uptake of peptides that bind the human transferrin receptor", Eur. J. Biochem., vol. 268, No. 7, 2001, pp. 2004-2012.
Mertsch et al., "4-Hydroxynonenal impairs the permeability of an in vitro rat blood-brain barrier", Neuroscience Letters, vol. 314, No. 3, 2001, pp. 135-138.
Muruganandam et al., "Selection of phage-displayed llama single-domain antibodies that transmigrate across human blood-brain barrier endothelium", The FASEB Journal express article, Dec. 28, 2001, pp. 1-22.
Pardridge, "Blood-Brain Barrier Drug Targeting: The Future of Brain Drug Development", vol. 3, Issue 2, pp. 90-105, 2003.
Parmley et al., "Antibody-selectable filamentous fd phage vectors: affinity purification of target genes", Gene, vol. 73, No. 2, 1988, pp. 305-318.
Reichel et al., "Carrier-Mediated Delivery of Metabotropic Glutamate Receptor Ligands to the Central Nervous System: Structural Tolerance and Potential of the L-system Amino Acid Transporter at the Blood-Brain Barrier", Journal of Cerebral Blood Flow & Metabolism, vol. 20, No. 1, 2000, pp. 168-174.
Reichel et al., "Evaluation of the RBE4 Cell Line to Explore Carrier-mediated Drug Delivery to the CNS Via the L-system Amino Acid Transporter At the Blood-Brain Barrier", Journal of Drug Targeting, vol. 10, No. 4, Jun. 2002, pp. 277-283.
Rist et al., "F-Actin cytoskeleton and sucrose permeability of immortalised rat brain microvascular endothelial cell monolayers: effects of cyclic AMP and astrocytic factors", Brain Research, vol. 768, No. 1-2, pp. 10-18, 1997.
Roux et al., "Rat Brain Endothelial Cell Lines for the Study of Blood-Brain Barrier Permeability and Transport Functions", Cellular and Molecular Neurobiology, vol. 25, No. 1, Feb. 2005, pp. 41-58.

(Continued)

*Primary Examiner* — Amber D Steele
(74) *Attorney, Agent, or Firm* — Birch, Stewart, Kolasch & Birch, LLP

(57) ABSTRACT

An isolated peptide including an amino acid sequence of SEQ ID NO: 1 is provided. The disclosure also provides a delivery system comprising a carrier having a surface, a drug or a dye encapsulated in the carrier, and the disclosed peptide (having an amino acid sequence of SEQ ID NO: 1) grafted on the surface of the carrier.

14 Claims, 7 Drawing Sheets

(56) References Cited

OTHER PUBLICATIONS

Schmauss et al., "In Vivo Studies on Spinal Opiate Receptor Systems Mediating Antinociception. II. Pharmacological Profiles Suggesting a Differential Association of Mu, Delta and Kappa Receptors with Visceral Chemical and Cutaneous Thermal Stimuli in the Rat", The Journal of Pharmacology and Experimental Therapeutics vol. 228 No. 1 1984 pp. 1-12.

Schröder et al., "Nanoparticles, a drug carrier system to pass the blood-brain barrier, permit central analgesic effects of i.v. dalargin injections", Brain Research, vol. 710, No. 1-2, 1996, pp. 121-124.

Schroeder et al., "Nanoparticle Technology for Delivery of Drugs Across the Blood-Brain Barrier", Journal of Pharmaceutical Sciences, vol. 87, No. 11, Nov. 1998, pp. 1305-1307.

Smith et al., "Libraries of Peptides and Proteins Displayed on Filamentous Phage", Methods in Enzymology, vol. 217, 1993, pp. 228-257.

NCBI GenBank Accession number: ECZ30490,"hypothetical protein GOS_2207008 [marine metagenome]," Apr. 6, 2007.

Taiwanese Office Action for corresponding application No. 099146311, dated Oct. 9, 2013.

* cited by examiner

PEPTIDE FOR TRANSMIGRATION ACROSS BLOOD BRAIN BARRIER AND DELIVERY SYSTEMS COMPRISING THE SAME

CROSS REFERENCE TO RELATED APPLICATIONS

This application claims the benefit of U.S. Provisional Application No. 61/291,334, filed on Dec. 30, 2009, the entirety of which is incorporated by reference herein.

BACKGROUND

1. Technical Field

The disclosure relates to a peptide, and more particularly to a peptide for transmigration across the blood brain barrier and a delivery system comprising the same.

2. Description of the Related Art

The blood brain barrier (BBB) is composed of brain endothelial cells capable of blocking foreign substances, such as toxins, to enter therethrough, due to tight junctions therebetween. However, hydrophobic or low-molecular-weight molecules can pass through the BBB via passive diffusion.

Some active compounds, for example, hydrophilic protein drugs for treating cerebral or nervous diseases, cannot enter brain tissue via passive diffusion due to their large molecular weight or hydrophilicity.

Accordingly, structural modification of drugs has been developed to increase hydrophobicity of drugs, allowing various active compounds to pass though the BBB. Other methods for allowing hydrophilic or macromolecular drugs to pass through the BBB includes, for example, absorption-mediated transport (AMT) allowing positive-charged carriers to pass through the BBB via charge absorption, carrier-mediated transcytosis (CMT) allowing hydrophilic metal ions such as $Na^+$ and $K^+$, di-peptides, tri-peptides or glucose to pass through the BBB via transporters, and receptor-mediated transcytosis (RMT) allowing macromolecules such as insulin, transferrin, or low-density lipoprotein (LDL) to pass through the BBB via transcytosis.

SUMMARY

One embodiment of the invention provides an isolated peptide comprising an amino acid sequence of SEQ ID NO: 1.

One embodiment of the invention provides a delivery system comprising a carrier having a surface, a drug or a dye encapsulated in the carrier, and an isolated peptide comprising an amino acid sequence of SEQ ID NO: 1 grafted on the surface of the carrier.

The disclosure provides a novel peptide ligand (BP02, having an amino acid sequence of SEQ ID NO: 1 KYLAYPDSVHIW) capable of targeting and transmigration across the blood brain barrier (BBB). The drug-encapsulated carrier grafted with the disclosed peptide ligand prevents drugs from being destroyed when attempting to enter the brain.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawing, wherein.

DETAILED DESCRIPTION

Figure 1:
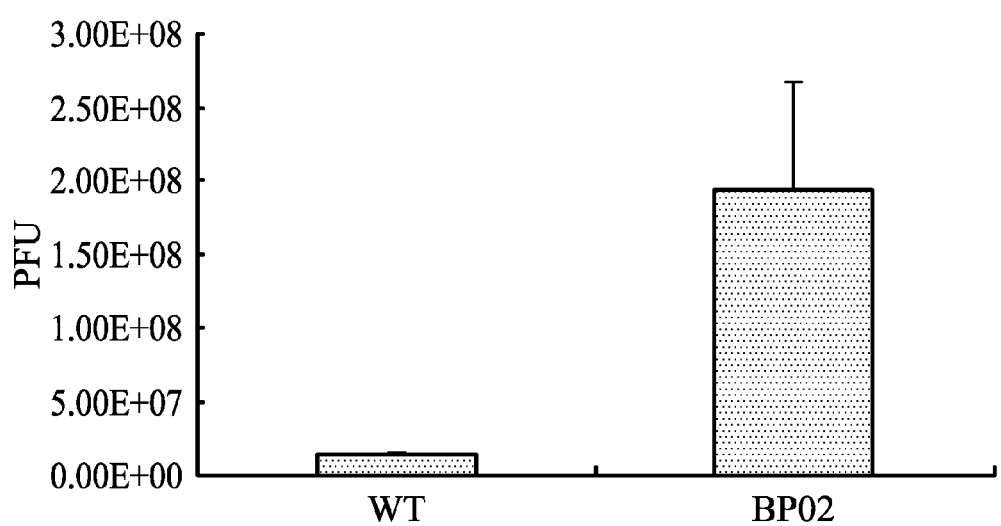
FIG. 1 is a functional assay of wild type and BP02 phages using a transwell system according to an embodiment of the invention.

The following description is of the best-contemplated mode of carrying out the invention. This description is made for the purpose of illustrating the general principles of the invention and should not be taken in a limiting sense. The scope of the invention is best determined by reference to the appended claims.

In an embodiment, an isolated peptide comprising an amino acid sequence of SEQ ID NO: 1 is provided.

The disclosed peptide may comprise an amino acid sequence of KYLAYPDSVHIW (SEQ ID NO: 1) consisting of 12 amino acid residues. The disclosed peptide specifically binds to the blood brain barrier (BBB) in vitro and in vivo.

A functional equivalent of the disclosed peptide is a peptide having an amino acid sequence at least 60% (e.g., 85%, 90% or 95%) identical to that of the disclosed peptide and possessing the same peptide activity as the disclosed peptide.

The percent identity of the two amino acid sequences is determined using the algorithm of Karlin and Altschul *Proc. Natl. Acad. Sci.* USA 87:2264-68, 1990, as modified in Karlin and Altschul *Proc. Natl. Acad. Sci.* USA 90:5873-77, 1993. Such an algorithm is incorporated in the BLASTN and BLASTX programs (version 2.0) of Altschul, et al. *J. Mol. Biol.* 215:403-10, 1990. BLAST protein searches can be performed with the BLASTX program, score=50, wordlength=3 to obtain amino acid sequences homologous to the protein molecule of the invention. Where gaps exist between two sequences, Gapped BLAST can be utilized as described in Altschul et al., *Nucleic Acids Res.* 25:3389-3402, 1997. When utilizing the BLAST and Gapped BLAST programs, the default parameters of the respective program (e.g., BLASTX and BLASTN) can be used.

The disclosed peptide may be prepared by a chemical synthesis method known in the art (Creighton, Proteins; Structures and Molecular Principles, W.H. Freeman and Co., NY, 1983). Typical examples of such a peptide synthesis method may include, but are not limited to, liquid-phase or solid-phase synthesis, fragment condensation, and F-MOC or T-BOC chemistry (Chemical Approaches to the Synthesis of Peptides and Proteins, Williams et al., Eds., CRC Press, Boca Raton Fla., 1997; and A Practical Approach, Atherton & Sheppard, Eds., IRL Press, Oxford, England, 1989).

Further, the disclosed peptide may be prepared by a genetic engineering technique. First, a DNA sequence encoding the aforesaid peptide is constructed according to a conventional method. The DNA sequence may be constructed by PCR amplification using appropriate primers. Alternatively, the DNA sequence may also be synthesized by a standard apparatus known in the art, for example, an automated DNA synthesizer (commercially available from Biosearch or Applied Biosystems). Then, the constructed DNA sequence is inserted into a vector comprising one or more expression control sequences (for example, promoters, enhancers, etc.) which are operatively linked to the DNA sequence. Note that the expression control sequences regulate the expression of the DNA sequence, and a host cell is then transformed with the resulting recombinant expression vector. The resulting transformants are cultured under a medium and culture conditions suitable to induce the expression of the DNA sequence. Then, a substantially pure peptide encoded by the DNA sequence is recovered from the cell culture. The recovery of peptide can be carried out by a conventional method known in the art (for example, chromatography). As used herein, the term "substantially pure peptide" means that the peptide according to the invention is substantially free from any other proteins derived from the host. The genetic engineering method for synthesis of the peptide of the invention can be found in the following literature: Maniatis et al., Molecular Cloning; A Laboratory Manual, Cold Spring Harbor Laboratory, 1982; Sambrook et al., Molecular Cloning: A-Laboratory Manual, Cold Spring Harbor Press, N.Y., Second (1998) and Third (2000) Edition; Gene Expression Technology, Methods in Enzymology, Genetics and Molecular Biology, Methods, in Enzymology, Guthrie & Fink (eds.), Academic Press, San Diego, Calif., 1991; and Hitzeman et al., J. Biol. Chem., 255:12073-12080, 1990.

The disclosure screens a blood brain barrier-specific peptide using a phage peptide display technique.

In an embodiment, a delivery system is provided. The delivery system comprises a carrier having a surface, a drug or a dye encapsulated in the carrier, and an isolated peptide comprising an amino acid sequence of SEQ ID NO: 1 grafted on the surface of the carrier.

The carrier may comprise nanoparticle, polymeric nanoparticle, solid liquid nanoparticle, polymeric micelle, liposome, microemulsion or liquid-based nanoparticle. In an embodiment, the liposome carrier is selected. The liposome may comprise a first lipid, a second lipid or cholesterol. The first lipid may be a phospholipid, for example, phosphatidyl choline (PC), soy phosphatidyl choline (SPC), hydrogenated soy phosphatidyl choline (HSPC) or phosphatidyl ethanolamine (PE). The second lipid may comprise dipalmitoyl phosphatidyl glycerol (DPPG) or distearoylphosphatidylethanolamine-polyethyleneglycol (DSPE-PEG). In the liposome composition, the first lipid has a mole percent of about 60-70, the second lipid has a mole percent of about 1-10 and the cholesterol has a mole percent of about 20-30, based on 100 mole percent of the carrier. In still another embodiment, the polymeric micelle carrier is selected. Micelles are formed when amphiphiles are placed in water. They consist of an inner core of assembled hydrophobic segments capable of solubilizing lipophilic substances and an outer hydrophilic corona serving as a stabilizing interface between the hydrophobic core and the external aqueous environment. The use of polymer-based micelles has gained much attention because of the high diversity of polymers, their biocompatibility, biodegradibility, and the multiplicity of functional groups they display for the conjugation of pilot molecules. Like their low-molecular-weight counterparts, amphiphilic polymers associate in water to form polymeric micelles, consisting of a hydrophobic core stabilized by a corona of hydrophilic polymeric chains exposed to the aqueous environment. Polymeric micelles can be used as efficient carriers for compounds, which alone exhibit poor solubility, undesired pharmacokinetics, and low stability in a physiological environment. The hydrophilic shell contributes greatly to the pharmaceutical behavior of polymeric formulations by maintaining the micelles in a dispersed state, as well as by decreasing undesirable drug interactions with cells and proteins through steric-stabilization effects. The size of polymeric micelles ranges from ~10 to ~100 nm, and usually the size distribution is narrow. They can increase drug bioavailability and retention, since the drug is well protected from possible inactivation under the effect of their biological surroundings. Polymeric micelles have been studied extensively as delivery medium for injectable drug formulations of poorly water-soluble drugs such as paclitaxel, indomethacin, amphotericin B, adriamycin, and dihydrotestosterone. Overall, they proved to be highly effective drug delivery vehicles.

The drug may comprise synthetic drugs, peptide drugs, protein drugs or nucleic acid drugs. The nucleic acid drug may comprise plasmid DNA, antisense oligonucleotide or RNAi.

The disclosed peptide may comprise an amino acid sequence of KYLAYPDSVHIW (SEQ ID NO: 1) consisting of 12 amino acid residues. The disclosed peptide specifically binds to the blood brain barrier (BBB) in vitro and in vivo.

The isolated peptide has a mole percent of about 0.1-5, based on 100 mole percent of the carrier.

The invention provides a novel peptide ligand (BP02, having an amino acid sequence of SEQ ID NO: 1 KYLAYPDSVHIW) capable of targeting and transmigration across the blood brain barrier (BBB). The drug-encapsulated carrier grafted with the disclosed peptide ligand prevents drugs from being destroyed and increases drug accumulation in brain.

Example 1

Establishment of an In Vitro Blood Brain Barrier Model

An in vitro blood brain barrier model was constructed by co-culture of RBE4 cells and C6 cells respectively on both sides of a collagen-treated semi-permeable membrane (Transwell-COL membrane, pore size 0.4 μm; Corning Costar, USA) formed on the bottom of a Transwell-COL insert inserted into each well of a 12-well plate to mimic physiological blood brain barrier conditions. Each well was divided into an apical compartment and a basal compartment by the Transwell-COL insert. First, C6 cells ($10^5$ cells/filter) were uniformly seeded on the back of the Transwell-COL membrane and C6 cells were allowed to adhere to the bottom side of the filter for one hour and then C6 cell culture medium [Ham' F10 supplemented with 15% horse serum, 2.5% fetal bovine serum (FBS) and penicillin/streptomycin (100 U/ml and 100 μg/ml, respectively)] was added to the inside (the apical compartment of the well) and outside (the basal compartment of the well) of the Transwell-COL insert. After cultivating for two days, the C6 cell culture medium was removed. A co-culture medium (pH 7.2) (a α-MEM: Ham' F-10 (1:1) mixing culture medium containing 10% FBS, 1 ng/ml bFGF and penicillin/streptomycin (100 U/ml and 100 μg/ml, respectively)) was then added to the basal compartment of the well. Next, RBE4 cells ($10^5$ cells/filter) were seeded on the inside side of the Transwell-COL membrane (within the apical compartment of the well) and cultivated with C6 cells in the 37° C. incubator (5% $CO_2$) for 6 to 7 days. The co-cultured medium was refreshed every two days.

Example 2

Estimation for Permeation of the In Vitro Blood Brain Barrier Model

After co-culture of RBE4 cells and C6 cells for 6 to 7 days, one co-cultured insert was used to confirm the tightness of the in vitro blood brain barrier model. First, the co-cultured medium was removed from the insert. The co-cultured insert was washed with HBSS buffer three times and incubated for 30 min in HBSS buffer at 37° C. After removal of the HBSS buffer, 1.5 ml of a fresh HBSS buffer was added to the basal compartment of the well and 0.5 ml of FLU solution (1 µg/ml in HBSS buffer) was then added to the apical compartment of the well for transportation for four hours at 37° C. Sample solution in each basal compartment was collected and a FLU fluorescent analysis ($\lambda_{ex}$=460 nm, $\lambda_{em}$=515 nm) (Intelligent Fluorescence Detector, FP2020, JASCO) was performed. Finally, the FLU permeability coefficient P (cm/min) was calculated using the following formula to ensure an in vitro blood brain barrier model with tight cell junction was formed ($P<8\times10^4$ cm/min).

$$P = \frac{dQ}{dt} \times \frac{1}{A \times C_0}$$

$\frac{dQ}{dt}$ = the amount of *FLU* transported per minute (*ng*/min)

A = the surface area of the filter (cm²)

$C_0$ = the initial concentration (*ng*/ml)

Example 3

BP02 Peptide Screening

A commercial Ph.D.-12™ phage-displayed peptide library with a complexity of 2.7×10⁹ was used for panning against RBE4 cells and transmigration screening with the in vitro BBB model. First, RBE4 cells were seeded in 6-well and incubate at 37° C. until confluence. Confluent RBE4 cell monolayer was washed with PBS buffer for three times and blocked with a BSA solution (5 mg/ml in PBS buffer) at 37° C. for 10 min. Phages from the library (1.5×10¹¹ pfu) were applied to the cells at 4° C. for two hours. The cells were washed with 0.1% TBST buffer (50 mM Tris-HCl, pH 7.4, 150 mM NaCl, 0.1% v/v Tween-20) for six times and bound phages were dislodged by the stripping washes (0.2M glycine-HCl, Ph 2.2) at 4° C. The eluate had to been neutralized immediately with 150 µl 1M Tris-HCl buffer (pH 9.0) (first panning) Phage from the eluate was amplified and purified as described elsewhere. Amplified phage from the first panning (1.5×10¹¹ pfu) was used for the second round of selection (second panning, as described in the section of first panning except the replacement of 0.1% TBST buffer with 0.3% TBST buffer). Phage screening for transmigration across the in vitro BBB model was started with the amplified phages from the second panning. The in vitro BBB model was constructed as described before. After the well was washed with HBSS buffer and incubated for 30 min in HBSS buffer, amplified phages from the second panning (7.0×10¹⁰ pfu) were applied to the apical compartment at 37° C. for four hours. Sample solution in the basal compartment was collected and transmigrated phages in the solution were amplified and purified (first transwell screening). The Second to third rounds of transwell screening (7.0×10¹⁰ pfu) were started with amplified phages from the basal compartment of previous transwell screening. Amplified phages from the third transwell screening were applied to RBE4 cells for another three continuous pannings. The selected phages from the last panning were amplified and sequenced. A novel peptide (BP02, having an amino acid sequence of SEQ ID NO: 1) was identified.

Example 4

Transmigration Rate Assay of BP02 Phages

After co-culture of RBE4 cells and C6 cells for 6 to 7 days, a transmigration rate assay for BP02 phages was performed. First, the co-cultured medium was removed from the co-cultured transwell. Each well was then washed with HBSS buffer three times and incubated for 30 min in HBSS buffer at 37° C. After removal of the HBSS buffer, a fresh HBSS buffer was added to the basal compartment of the well. Wild type phages and BP02 phages (about 10¹¹ pfu/insert) were respectively added to the apical compartment of the well for transmigration for one hour at 37° C. 20 µl of a sample solution in the basal compartment was then collected and 10-fold serial dilutions were prepared for phage titering to calculate the transmigration rate of the phage. The results are shown in FIG. 1. The transmigration rate of BP02 phage is 14.8 folds of control (wild type) phage.

Example 5

RBE4 Cell Binding Assay of BP02 Phages (by OPD Chromophore Substrate Method)

Figure 2:
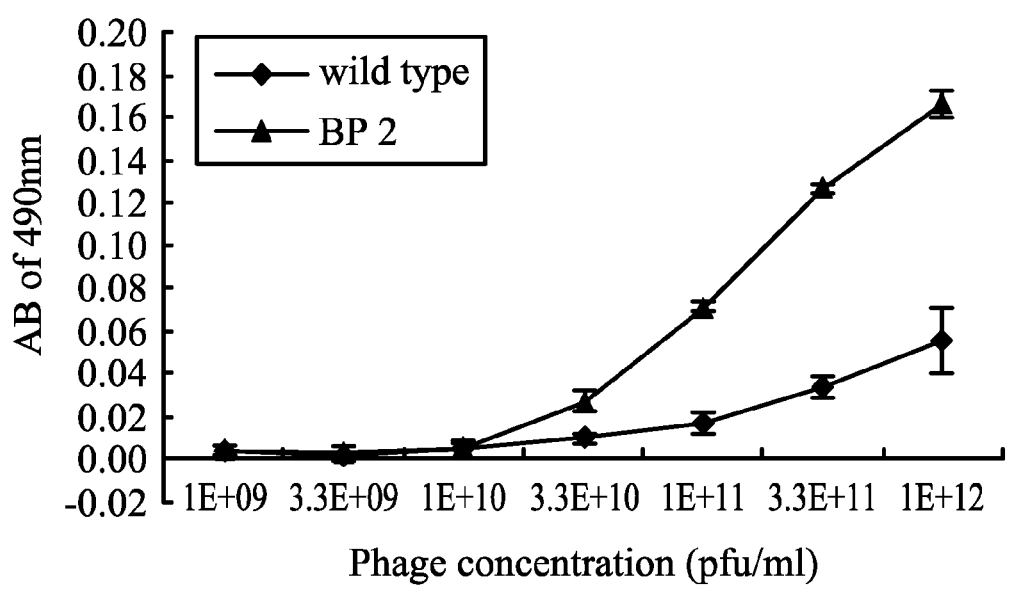
FIG. 2 is RBE4 cell binding of wild-type and BP02 phages according to an embodiment of the invention.

Collagen I was coated on a 96-well plate (37° C., one hour). RBE4 cells (10⁴ cells/well) was then cultivated in the collagen-coated 96-well plate. After two days, the cells were washed with a PBS buffer twice to completely remove a fetal bovine serum (FBS). Wild type phages and BP02 phages were respectively added to the cells for interaction for one hour at 37° C. After washing the cells with a PBS buffer for three times, the cells were fixed (room temperature, 10 minutes) using 3% formaldehyde. After washing the cells with a PBS buffer for four times, HRP-conjugated anti-M13 mAb (1:1000) was added thereto for interaction for one hour at 37° C. After washing the cells with a PBS buffer for four times, an OPD chromophore solution was added thereto for reaction at 37° C. until brown color appears (about two hours). The OD value of the resulting solution was measured at a wavelength of 490 nm by an ELISA reader. The results are shown in FIG. 2. The results showed the binding of BP02 phages to RBE4 cells occurs in a dose-dependent manner. In addition, no or slight reactivity was found with the control (wild type) phages.

Example 6

RBE4 Cell Binding Assay of BP02 Phages (by Fluorophore Tyramide Substrate Method)

Collagen I was coated on coverslips in a 12-well plate (37° C., one hour). RBE4 cells (1×10⁵ cells/well) was then cultivated on the collagen-coated coverslips in a 12-well plate. After one day, the cells were washed with a PBS buffer twice to completely remove a fetal bovine serum (FBS). The cells were then fixed (room temperature, 10 minutes) using 4% formaldehyde. After washing the cells with a PBS buffer twice, 1% $H_2O_2$ was added to the cells to quench the cell culture to reduce endogenous activity (room temperature, 10 minutes). After washing the cells with a PBS buffer twice, 1% BSA buffer was added to the cells to block the cells (room temperature, 30 minutes). Wild type phages and BP02 phages (10¹² pfu/well) were then respectively added to the cells for interaction for one hour at room temperature. After washing the cells with a PBS for three times, HRP-conjugated anti-M13 mAb (1:5000) was added to the cells for interaction for one hour at room temperature. After washing with a PBS buffer for three times, a fluorophore tyramide working solution was added to the cells for reaction for 10 minutes at room temperature. After washing with a PBS buffer for three times, the cells were mounted and photographed by a fluorescent microscope. The images showed that the binding affinity of BP02 phages to RBE4 cells was very strong. The control (wild type) phages could not bind to RBE4 cells.

Example 7

Preparation of Rhodamine-PE Labeled BP02 Liposomes (1) Preparation of Rhodamine-PE Labeled Liposomes 70 mol % of soy phosphatidyl choline (SPC), 30 mol % of cholesterol, 2 mol % of distearoylphosphatidylethanolamine-polyethyleneglycol (DSPE-PEG2000), 1 mol % of rhodamine-PE and 3 ml of chloroform were mixed in a round-bottom flask. After removal of chloroform by a rotary evaporator, a lipid thin-film product was formed in the flask. Next, PBS buffer was added to hydrate the lipid thin-film and the hydrate was dispersed by sonication. The dispersed product was then sized by an extruder (respectively using 200 nm, 100 nm and 50 nm filters) at a temperature of 60° C. to form rhodamine-PE labeled liposomes. The extrusion process was performed 10 times for each filter. The particle size (PS) of the liposomes was 100±20 nm.

(2) Preparation of DSPE-PEG2000-BP02

3.2 mg of cysteine-BP02 was dissolved in 10 mM phosphate buffer (pH 6.5) to form a cysteine-BP02 solution (2 mM). 5.9 mg of distearoylphosphatidylethanolamine-polyethyleneglycol maleimide (DSPE-PEG-maleimide) was dissolved in 10 mM phosphate buffer (pH 6.5) to form a DSPE-PEG-maleimide solution (2 mM). The DSPE-PEG-maleimide solution was slowly added to the cysteine-BP02 solution (molar ratio=1:1) at 4° C. and stirred for four hours to prepare DSPE-PEG2000-BP02. The grafting yield thereof was 61%, measured by 5,5'-dithiobis-(2-nitrobenzoic acid) (DTNB, Ellman's reagent).

(3) Preparation of Rhodamine-PE Labeled BP02 or PEGylated Liposomes 3 mol % of the DSPE-PEG2000-BP02 solution and 3 mol % of the DSPE-PEG2000 solution were respectively added to the liposome solution for post-insertion for one hour under a 60° C. water bath. Rhodamine-PE labeled BP02 liposomes and Rhodamine-PE labeled PEGylated liposomes were prepared.

Example 8

RBE4 Cell Binding Assay of Rhodamine-PE Labeled BP02 Liposomes

Collagen I was coated on coverslips in a 12-well plate (37° C., one hour). RBE4 cells ($1 \times 10^5$ cells/well) was then cultivated on the collagen-coated coverslips in a 12-well plate. After one day, the cells were washed with PBS buffer twice and rhodamine-PE labeled BP02 liposomes and rhodamine-PE labeled PEGylated liposomes (2 μg/ml rhodamine-PE) were then respectively added to the cells for interaction for two hours at 37° C. After washing the cells with a PBS buffer for three times, the image was photographed by a fluorescent microscope.

In accordance with the fluorescent photographs, RBE4 cells bound with the rhodamine-PE labeled BP02 liposomes exhibited stronger fluorescence than RBE4 cells bound with the rhodamine-PE labeled liposomes. That is, the rhodamine-PE labeled BP02 liposomes generated a strong binding capability with RBE4 cells and were rapidly endocytosed by RBE4 cells through the BP02 ligand.

Example 9

Preparation of FLU-Encapsulated BP02 Liposomes 70 mol % of SPC, 30 mol % of cholesterol and 3 ml of chloroform were mixed in a round-bottom flask. After removal of chloroform by a rotary evaporator, a lipid thin-film product was formed in the flask. Next, 50 mM FLU solution (in PBS buffer) was added to hydrate the lipid thin-film and the hydrate was dispersed by sonication. The dispersed product was then sized by an extruder (respectively using 200 nm, 100 nm and 50 nm filters) at a temperature of 60° C. to form FLU-encapsulated liposomes. The extrusion process was performed 10 times for each filter. Free FLU dyes were removed and the FLU-encapsulated liposomes were purified by a gel filtration method. The particle size (PS) of the liposomes was 100±20 nm. Furthermore, 3 mol % of the DSPE-PEG2000-BP02 solution and 3 mol % of the DSPE-PEG2000 solution were respectively added to the liposome solution for post-insertion for one hour under a 60° C. water bath. FLU-encapsulated BP02 liposomes and FLU-encapsulated PEGylated liposomes were prepared and kept in dialysis bags (MWCO=1000 Da) to remove residual dyes.

Example 10

Permeation Rate Assay of Flu-Encapsulated BP02 Liposomes

Figure 3:
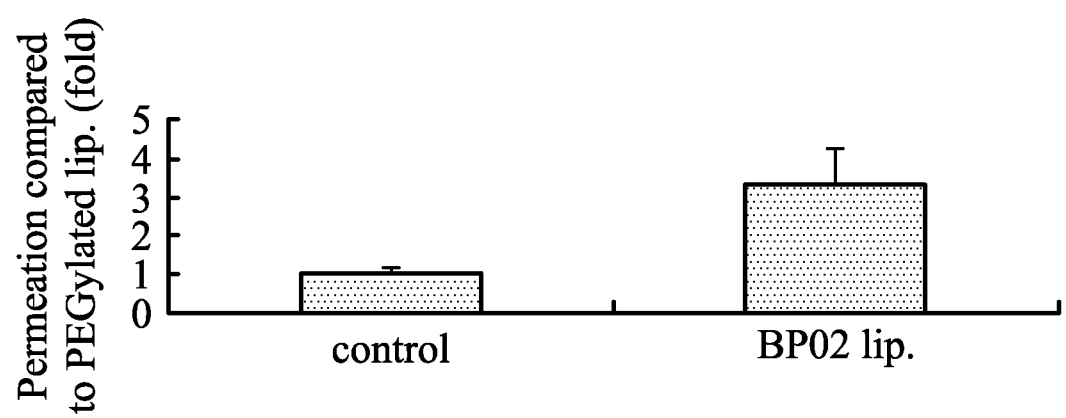
FIG. 3 is transmigration of BP02 peptide-modified FLU-encapsulated liposomes according to an embodiment of the invention.

After co-culture of RBE4 cells and C6 cells for 6 to 7 days, a permeation rate assay for FLU-encapsulated BP02 liposomes was performed. First, the co-cultured medium was removed from the co-cultured transwell. Each well was then washed with HESS buffer three times and incubated for 30 min in HBSS buffer at 37° C. After removal of the HBSS buffer, a fresh HESS buffer was added to the basal compartment of the well. FLU-encapsulated BP02 liposomes and FLU-encapsulated PEGylated liposomes (about 150 ng/ml) were then respectively added to the apical compartment of the well for transportation for one hour at 37° C. Respective sample solutions in the basal compartment was then collected and diluted 10 times with methanol. After destroying the liposomes with methanol, a FLU fluorescent analysis ($\lambda_{ex}$=460 nm, $\lambda_{em}$=515 nm) (Intelligent Fluorescence Detector, FP2020, JASCO) was performed and the permeation rate was calculated. The permeation rate of the FLU-encapsulated BP02 liposomes was 3.3 folds compared to the FLU-encapsulated PEGylated liposomes indicating that the BP02 ligand facilitated the liposomes transmigration across the blood brain barrier, as shown in FIG. 3.

Example 11

Preparation of Cy5.5-Encapsulated BP02 Liposomes 41.7 mg of SPC, 4.2 mg of hydrogenated soy phosphatidyl choline (HSPC), 4.1 mg of dipalmitoyl phosphatidyl glycerol (DPPG), 2.1 mg of cholesterol, 7.8 mg of Brij 76 (surfactant), 15.4 mg of DSPE-PEG2000 and 5 mg of Cy5.5 dye were dissolved in 5 ml of ethanol under a 60° C. water bath in a 25 ml reduced pressure concentrator to form a mixing solution. After reduced pressure concentration of the mixing solution, 5 ml of a sucrose solution (10%) was added to the mixing solution to form a hydrate. The hydrate was then dispersed by ultrasonic shaking at a temperature of 4° C. After filtering the hydrate (respectively using 0.45 μm and 0.2 μm filters), Cy5.5-encapsulated PEGylated liposomes were prepared (CYL003). Furthermore, the DSPE-PEG2000-BP02 (0.178 mg) solution was then added to CYL003 for reaction for one hour under a 60° C. water bath. Cy5.5-encapsulated BP02 liposomes (BP02-3.6%) were prepared.

Example 12

Biodistribution Assay of Cy5.5-Encapsulated BP02 Liposomes

Figure 4:
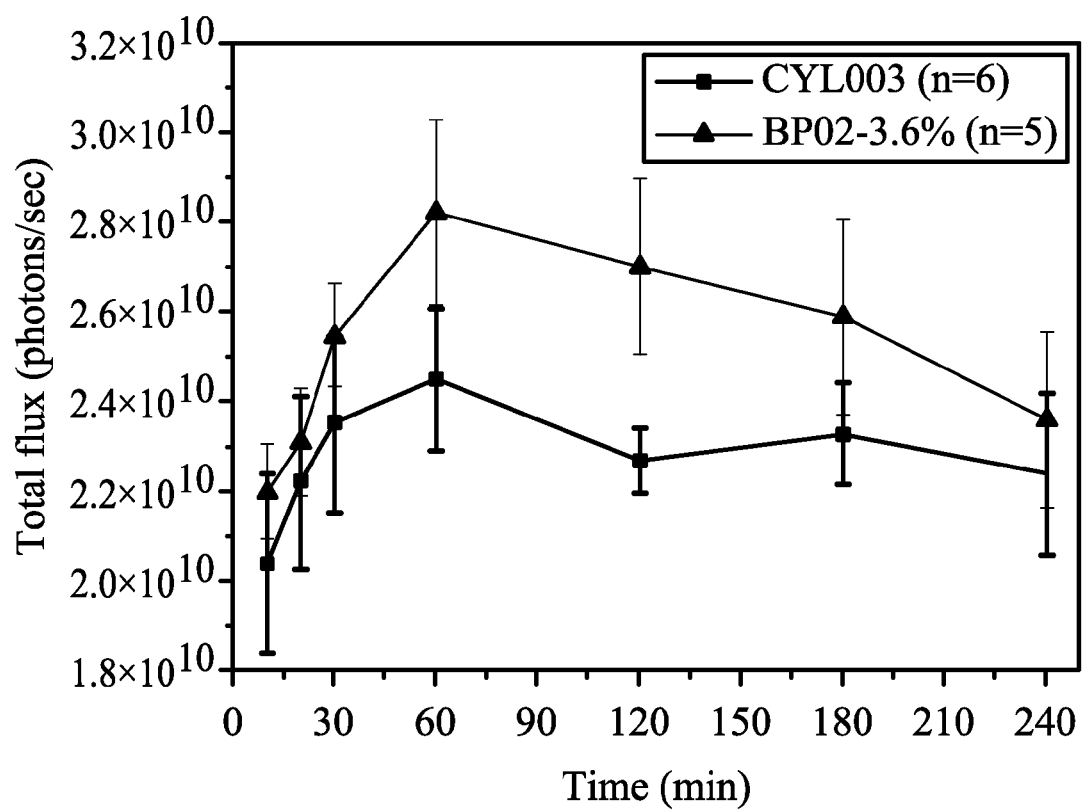
FIG. 4 is biodistribution of Cy5.5 encapsulated BP02 liposomes according to an embodiment of the invention.

A near infrared (NIR) fluorescent dye, Cy5.5 Phosphoramidite (GE Healthcare Life Sciences) was encapsulated into BP02 liposomes or PEGylated liposomes as an optical agent for imaging the biodistribution and the fluorescence intensity in the brain. The mice (4-6 weeks BALB/c nude mice) were injected via tail vein with 5 mg/kg Cy5.5 liposome, anesthetized by isoflurane inhalation, and imaged at 10, 20, 30, 60, 120, 180 and 240 mins post injection. Images were acquired by the IVIS200 system (Xenogen Corp.) using a one-second exposure time (f/stop=8, Binning=8), and the regions of interest (ROI) covering the entire brain as circled were analyzed by using Living Image and IGOR software. Fluorescence intensity was normalized by the initial fluorescence of each animal at 10 min postinjection and defined as photons per second per centimeter square per steradian ($p/s/cm^2/sr$). The results are shown in FIG. 4. The results indicated that the BP02 ligand facilitated the liposome accumulation in the brain of the mouse.

Example 13

Preparation of Endomorphin-1 Encapsulated BP02 Liposomes

For the analgesic studies, a mixture of SPC, HSPC, DPPG, cholesterol, Brij76, and TPGS at a 20:2:2:2:4:1 molar ratio was used to encapsulate a given drug loading of endomorphin-1 (EM-1). All materials were placed in a 12.5 ml $ZrO_2$ mortar and five $ZrO_2$ beads (10 mm of diameter) were added into the mortar to start the milling process at 500 rpm for one hour (Planetary Micro Mill, Pulverisette 7). The sticky paste was then hydrated with 10 mM PBS (pH 7.4) and stirred under room temperature for one hour. EM-1 encapsulated liposomes were prepared. Furthermore, 1.5 mol % of the DSPE-PEG2000-BP02 solution and 1.5 mol % of the DSPE-PEG2000 solution were respectively added to the liposome solution for post-insertion at 4° C. for overnight. EM-1 encapsulated BP02 liposomes (NL563-BP02) and EM-1 encapsulated PEGylated liposomes (NL563) were prepared.

Example 14

Hot Plate Test (PD Study)

To prove the brain-targeting, the animal model of hot-plate test was used to evaluate the analgesic efficacy of BP02 ligand. Hot-plate test was used to evaluate thermal pain reflexes due to footpad contact with a heated surface. The response of the animals to the hot plate reflects a nociceptive behavior, which involves complex circuit integration in the central nervous system.

Briefly, the mice were individually placed on a 55 hot plate apparatus and the time until onset of licking the hindlimb was measured. Basal latency was approximate 2 sec, and cut-off time in the absence of a response (T2) was set at 45 sec. The inhibition of the hindlimb-licking responses were expressed as percent maximal possible effect (% MPE) which was calculated as $[(T1-T0)/(T2-T0)] \times 100$, where T0 and T1 were the hot-plate latencies before and after intravenous injection of the EM-1 formulations. The hot-plate latency was determined 10, 20, 30, 60, 120, 180 and 210 min after the formulation injection (7.5 mg/kg EM-1), and the AUC (the area under a curve) values for MPE % versus time (min) plots were calculated.

Figure 5:
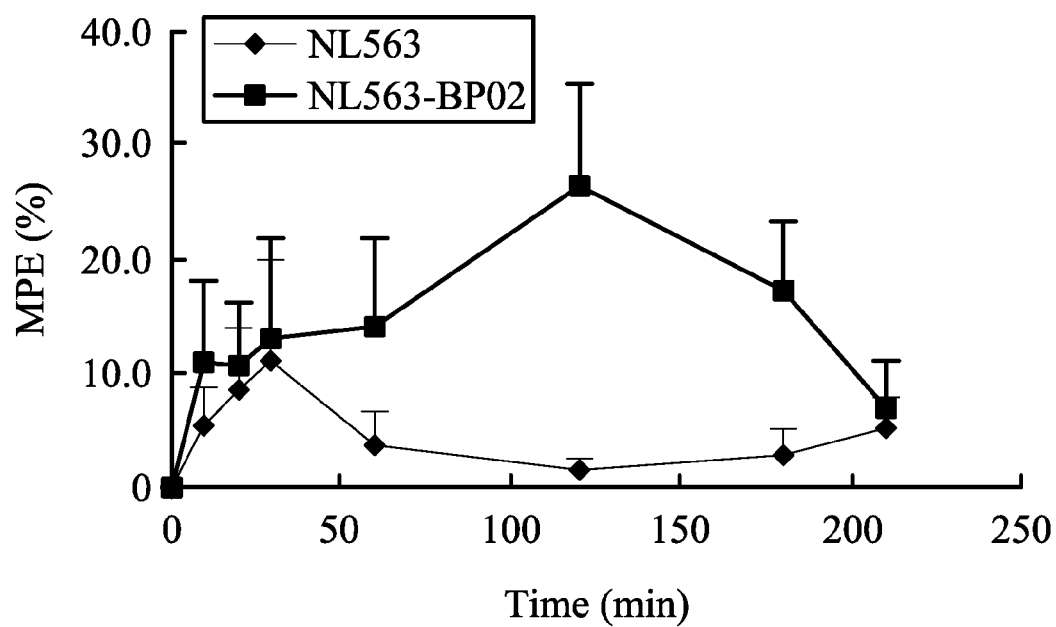
FIG. 5 is MPE % versus time (min) of PEGylated liposomes (NL563) and BP02 liposomes (NL563-BP02) according to an embodiment of the invention.
Figure 6:
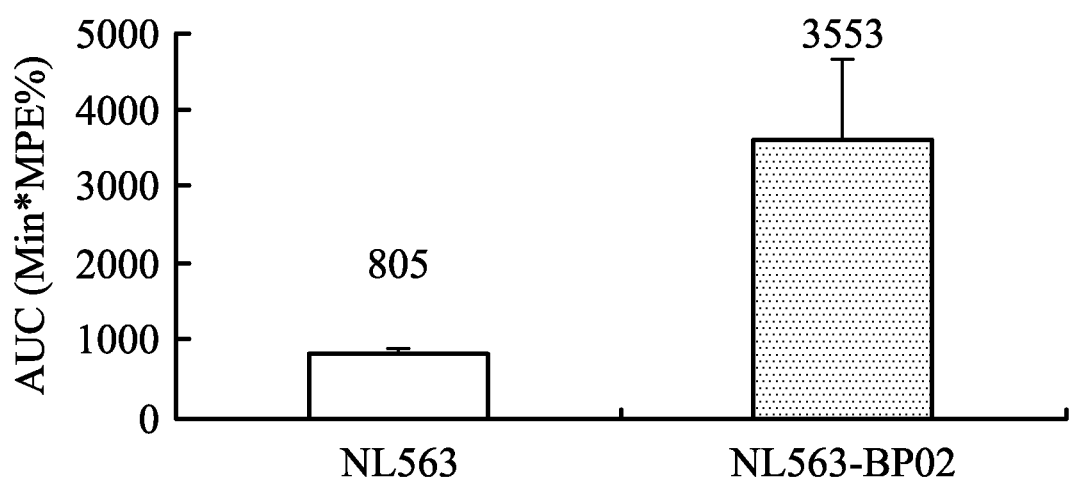
FIG. 6 is AUC (the area under a curve) values of PEGylated liposomes (NL563) and BP02 liposomes (NL563-BP02) according to an embodiment of the invention.

EM-1 given alone at a dose of 7.5 mg/kg did not reduce the nociceptive responses of mice (data not shown). The NL563 formulation at the same dose only had slight analgesic effect at 30 min post-dose. However, the NL563-BP02 formulation significantly evoked an analgesic activity, which reached an enhancement of hot plate latency by about 25% 120 min after administration and prolonged its analgesic activity longer than 3 hr. The efficacy of NLG563-BP02 was 4-fold higher than NL563 according to the AUC values, and there were significant differences between the formulations at 120 min and 180 min post-doses ($P<0.05$, one-tail t-test), indicating the targeting formulation (NLG563-BP02) could prevent drug degradation during the circulation and might help to deliver the drugs into the central nervous system, as shown in FIGS. 5 and 6.

Example 15

Preparation of Rhodamine-PE Labeled BP02 Polymeric Micelles (1) Preparation of DSPE-PEG5000-BP02

1 mg of cysteine-BP02 was dissolved in 10 mM phosphate buffer (pH 6.5) to form a cysteine-BP02 solution (0.625 mM). 3.7 mg of distearoylphosphatidylethanolamine-polyethyleneglycol maleimide (DSPE-PEG5000-maleimide) was dissolved in 10 mM phosphate buffer (pH 6.5) to form a DSPE-PEG5000-maleimide solution (0.625 mM). The DSPE-PEG5000-maleimide solution was slowly added to the cystine-BP02 solution (molar ratio=1:1) at 4° C. and stirred for overnight to prepare DSPE-PEG5000-BP02. The grafting yield thereof was 81%, measured by 5,5'-dithiobis-(2-nitrobenzoic acid) (DTNB, Ellman's reagent).

(2) Preparation of Rhodamine-PE Labeled BP02 Polymeric Micelles 10 mg of PEOZ-PLA copolymer (MW=15,000) and 0.05 mg of rhodamine-PE (Rh-PE) were mixed and dissolved in 1 ml chloroform. Chloroform was removed and the thin film obtained was rehydrated with 1 ml 10 mM PBS (pH 7.4) and sonicated for 1 min (XL2020, Misonix Inc., USA) to obtain rhodamine-PE labeled polymeric micelles (control). The 5% molar ratio DSPE-PEG5000-BP02 was additionally inserted in micelles as BP02 polymeric micelles. The particle sizes of the control and BP02 formulations were average 57.3 nm and 66.9 nm, respectively, measured by Laser particle size analyzer (N4 plus, Coulter Electronics, USA).

Example 16

In Vitro BP02 Polymeric Micelle Binding/Uptake by RBE4 Cells

In order to demonstrate the targeting ability of BP02 peptides on other nanoparticles, rhodamine-labeled polymeric micelles (PMs) with the coupling of BP02 peptides were formulated for the cellular binding/uptake study as well. RBE4 cells were first seeded on collagen I-coated coverslips and incubated overnight at 37° C. Control or BP02 PMs were applied to RBE4 cells and incubated in serum-free medium at 37° C. for 1 hr. After the incubation, the cells were washed three times with PBS and mounted for fluorescence microscopy. There is a significant increase in the cell-associated fluorescence for the cells treated with BP02 polymeric micelles, indicating their higher binding affinities to RBE4 cells.

Example 17

Quantification of BP02 Polymeric Micelle Binding/Uptake by RBE4 Cells

Figure 7:
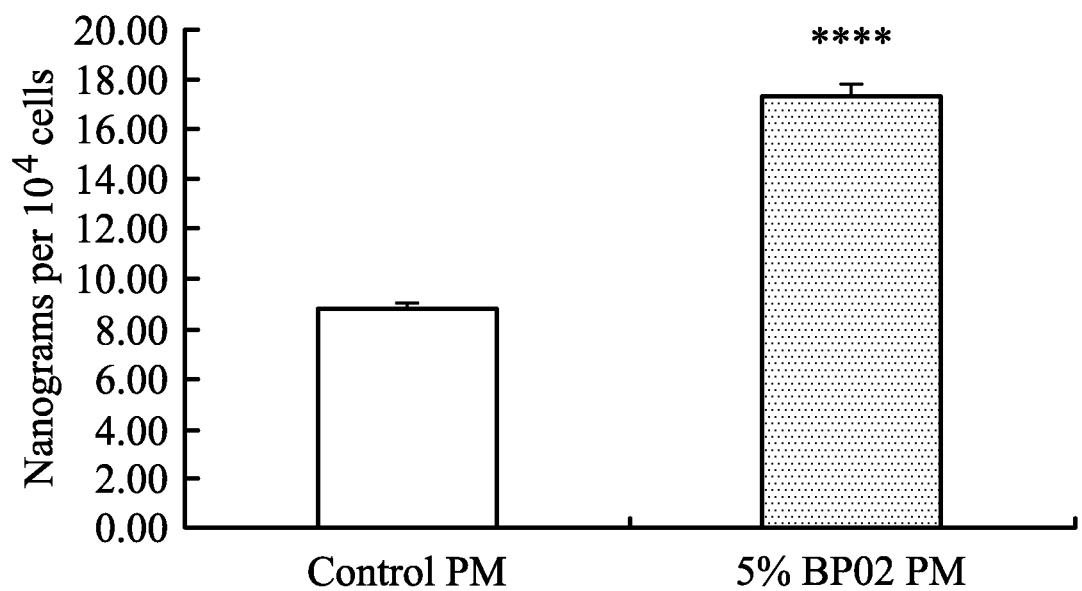
FIG. 7 is quantification of BP02 polymeric micelle binding/uptake by RBE4 cells according to an embodiment of the invention.

The cellular binding/uptake of rhodamine-labeled polymeric micelles was quantified. Briefly, RBE4 cells were seeded into collagen I-coated 12-well plates at densities of $2 \times 10^5$ cells/well and incubated at 37° C. for 2 days. Control or BP02 PMs at a concentration of 1.25 µg/ml equivalent Rh-PE were added and incubated in serum-free medium at 37° C. for 1 hr. The medium was aspirated and the cells were rinsed three times with cold PBS. Then the cells were lysed with cell lysis buffer (ProteoJET™ Mammlian Cell Lysis reagent, K0301, Fermentas), and Rh-PE concentrations in the cell lysates were measured with a fluorescence spectrophotometer (Intelligent Fluorescence Detector, FP2020, JASCO) at an excitation wavelength of 568 nm and an emission wavelength of 590 nm. On the other hand, the cells in one well were harvested and the cell number was counted. Cellular binding/uptake is expressed as nanograms per $10^4$ cells. There is a significant increase in the cell-associated fluorescence for the cells treated with BP02 PMs when compared to control PMs ($P<0.00005$, two-tail t-test), as shown in FIG. 7.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An isolated peptide comprising at least 85% identity of the amino acid sequence of SEQ ID NO: 1.

2. The isolated peptide as claimed in claim 1, wherein the isolated peptide comprises at least 90% identity of the amino acid sequence of SEQ ID NO: 1.

3. The isolated peptide as claimed in claim 1, wherein the isolated peptide comprises at least 95% identity of the amino acid sequence of SEQ ID NO: 1.

4. A delivery system, comprising:
a carrier having a surface;
a drug or a dye encapsulated in the carrier; and
an isolated peptide as claimed in claim 1 grafted on the surface of the carrier.

5. The delivery system as claimed in claim 4, wherein the carrier comprises a nanoparticle, a polymeric nanoparticle, a solid liquid nanoparticle, a polymeric micelle, a liposome, a microemulsion, or a liquid-based nanoparticle.

6. The delivery system as claimed in claim 5, wherein the liposome comprises a first lipid, a second lipid and/or cholesterol.

7. The delivery system as claimed in claim 6, wherein the first lipid is a phospholipid.

8. The delivery system as claimed in claim 7, wherein the phospholipid comprises phosphatidyl choline (PC), soy phosphatidyl choline (SPC), hydrogenated soy phosphatidyl choline (HSPC) or phosphatidyl ethanolamine (PE).

9. The delivery system as claimed in claim 6, wherein the second lipid comprises dipalmitoyl phosphatidyl glycerol (DPPG) or distearoylphosphatidylethanolamine-polyethyleneglycol (DSPE-PEG).

10. The delivery system as claimed in claim 6, wherein the first lipid has a mole percent of 60-70, the second lipid has a mole percent of 1-10 and the cholesterol has a mole percent of 20-30, based on 100 mole percent of the carrier.

11. The delivery system as claimed in claim 4, wherein the drug comprises synthetic drugs, peptide drugs, protein drugs or nucleic acid drugs.

12. The delivery system as claimed in claim 11, wherein the nucleic acid drug comprises plasmid DNA, antisense oligonucleotide or RNAi.

13. The delivery system as claimed in claim 4, wherein the isolated peptide has a mole percent of 0.1-5, based on 100 mole percent of the carrier.

14. The delivery system as claimed in claim 4, wherein the isolated peptide has a mole percent of 0.1-2.5, based on 100 mole percent of the carrier.

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide

<400> SEQUENCE: 1

Lys Tyr Leu Ala Tyr Pro Asp Ser Val His Ile Trp
1               5                   10
```

* * * * *